US012651649B2

(12) United States Patent
Kwong et al.

(10) Patent No.: US 12,651,649 B2
(45) Date of Patent: Jun. 9, 2026

(54) REINFORCEMENT-LEARNING-BASED NETWORK TRANSMISSION OF COMPRESSED GENOME SEQUENCE

(71) Applicant: CITY UNIVERSITY OF HONG KONG, Kowloon (HK)

(72) Inventors: Sam Tak Wu Kwong, Kowloon (HK); Shiqi Wang, Kowloon (HK); Xiaona Li, Kowloon (HK); Zhenhao Sun, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 80 days.

(21) Appl. No.: 18/291,916

(22) PCT Filed: Nov. 27, 2023

(86) PCT No.: PCT/CN2023/134440
§ 371 (c)(1),
(2) Date: Jan. 24, 2024

(87) PCT Pub. No.: WO2024/114597
PCT Pub. Date: Jun. 6, 2024

(65) Prior Publication Data
US 2025/0095789 A1 Mar. 20, 2025

Related U.S. Application Data

(60) Provisional application No. 63/429,796, filed on Dec. 2, 2022.

(51) Int. Cl.
*G16B 50/50* (2019.01)
*G16B 40/00* (2019.01)
*H03M 7/30* (2006.01)

(52) U.S. Cl.
CPC ............ *G16B 50/50* (2019.02); *G16B 40/00* (2019.02); *H03M 7/6011* (2013.01); *H03M 7/70* (2013.01)

(58) Field of Classification Search
CPC ..... G16B 50/50; G16B 40/00; H03M 7/6011; H03M 7/70
See application file for complete search history.

(56) References Cited

U.S. PATENT DOCUMENTS

| 5,255,345 A | * | 10/1993 | Shaefer | .................. | G06Q 10/04 |
| | | | | | 706/13 |
| 2011/0285557 A1 | * | 11/2011 | Korodi | ................ | H03M 7/4006 |
| | | | | | 341/52 |

(Continued)

FOREIGN PATENT DOCUMENTS

| CN | 106910351 A | * | 6/2017 | ............. | G06N 3/045 |
| CN | 110678929 A | * | 1/2020 | ............. | G16B 50/50 |

(Continued)

*Primary Examiner* — Chico A Foxx
(74) *Attorney, Agent, or Firm* — Conley Rose, P.C.

(57) ABSTRACT

A framework that comprises a reinforcement-learning-based neural-network for compressing, and for transmitting the compressed genomes over a data network in repeated steps each of a plurality of species. The framework also takes data on inefficient transmission of compressed genome in the preceding step, and feeds this data forward to modify the selection of the compression parameter in the present step. The invention provides the possibility that the genome of any species may be compressed optimally and transmitted in optimal efficiency. That is, big genome sequence is neither over compressed, which takes a lot of processing time leading to delays, nor under compressed which will require more time to transmit.

4 Claims, 9 Drawing Sheets

(56)                    References Cited

U.S. PATENT DOCUMENTS

| | | | |
|---|---|---|---|
| 2014/0357993 A1 * | 12/2014 | Hiriyannaiah | H04N 19/12 |
| | | | 600/437 |
| 2016/0283407 A1 * | 9/2016 | Van Rooyen | G16H 10/60 |
| 2017/0270245 A1 * | 9/2017 | van Rooyen | G16B 50/40 |
| 2018/0121601 A1 * | 5/2018 | Hahm | G16B 50/30 |
| 2020/0185058 A1 * | 6/2020 | Song | G16B 30/00 |
| 2021/0201163 A1 * | 7/2021 | Kalsi | G06F 15/78 |
| 2021/0232775 A1 * | 7/2021 | Zhang | G06F 40/56 |
| 2024/0072825 A1 * | 2/2024 | Cooper | H03M 7/6035 |
| 2025/0131273 A1 * | 4/2025 | Mariooryad | G06N 3/092 |
| 2025/0190400 A1 * | 6/2025 | Li | G06F 16/1744 |

FOREIGN PATENT DOCUMENTS

| | | | | | |
|---|---|---|---|---|---|
| CN | 112051735 | A | * | 12/2020 | G05B 13/027 |
| CN | 113988266 | A | * | 1/2022 | G06N 3/045 |
| CN | 115098455 | A | * | 9/2022 | G16B 40/00 |
| CN | 115579058 | A | * | 1/2023 | G01B 20/20 |
| CN | 116107210 | A | * | 5/2023 | G05B 13/042 |
| CN | 111028897 | B | * | 6/2023 | G16C 20/90 |
| CN | 110999513 | B | * | 8/2023 | H04W 76/10 |
| CN | 117809742 | A | * | 4/2024 | G06N 3/0895 |
| EP | 1158740 | B1 | * | 9/2009 | H04L 9/40 |
| EP | 2381686 | A1 | * | 10/2011 | H04N 19/61 |
| EP | 2408114 | A2 | * | 1/2012 | H04N 19/91 |
| IN | 202231006793 | A | * | 3/2022 | |
| JP | 3871359 | B2 | * | 1/2007 | |
| WO | WO-9513661 | A1 | * | 5/1995 | H03M 7/30 |
| WO | WO-2021174484 | A1 | * | 9/2021 | H04L 1/0061 |

* cited by examiner

301

305

203 input      the method for compression      output input layer   hidden layer   output layer

REINFORCEMENT-LEARNING-BASED NETWORK TRANSMISSION OF COMPRESSED GENOME SEQUENCE

CROSS-REFERENCE TO RELATED APPLICATIONS

The present application is a filing under 35 U.S.C. 371 as the National Stage of International Application No. PCT/CN2023/134404, filed Nov. 27, 2023, entitled "REINFORCEMENT-LEARNING-BASED NETWORK TRANSMISSION OF COMPRESSED GENOME SEQUENCE," which claims the benefit of U.S. Provisional Application No. U.S. 63/429,796 filed 2 Dec. 2022; the content of both applications are incorporated herein by reference in their entirety.

FIELD OF INVENTION

The present invention relates to the field of bioinformatics. In particular, the invention relates to a method of generating or selecting a more suitable compression parameter, based on transmission conditions.

BACKGROUND OF THE INVENTION

The genome of any species can be sequenced and saved as a file to be transmitted through a computer network to relevant parties. However, large genomes contain so much information that the files are often too big to be transmitted fully within acceptable time frames. Typically, a large data file would be compressed into a smaller file before transmission, because smaller files transmit more quickly. However, compression of a large genome file is itself such a time consuming process, that it has rendered meaningless any improvement in the speed of transmission by file compression.

The problem is compounded by the rapid development of genome sequencing technology, which has led to reduction in costs of genome sequencing and an abundance of genome sequences. However, these are not accompanied by improvements in data transmission technology. Therefore, the flood of demands for genomic data is not met timely; and genome sequence inaccessibility has become the bottleneck that holds back the biotechnological and molecular biological industries.

Bandwidth is always changing. For any given piece of big genome sequence at any point in time, it is difficult to decide whether that piece of data would be transmitted faster after sacrificing more time to compress the data to a greater extent, or whether it would be faster to transmit the minimally compressed data.

Thus, it is desirable to propose a method of determining how to divide resources between the processes of compression and transmission of biodata, such that transmission of and access to such data is optimized.

SUMMARY OF THE INVENTION

The a first aspect, the invention proposes a method of transmitting a genome sequence among a series of genome sequence, comprising the steps of:

a) obtaining data of the network condition during a transmission of compressed form of a first genome sequence precedent in the series;

b) selecting a compression algorithm or modifying an compression parameter based on the data of the network condition; which includes supplying the data of the network condition to a neural network; such that the neural network selects the compression parameter or modifies the compression algorithm;

the neural network trained using training data that includes variables of past transmissions;

the variables of each past transmission include at least the following:

the network conditions of transmitting the compressed genome sequence;

'compression algorithm used to compress the genome sequence;

the size of the compressed genome sequence.

c) compressing a second genome sequence which is next in the series using the selected or modified compression parameter, to obtain a compressed form of the second genome sequence; and d) transmitting the compressed form of the second set genome;

e) adapting the neural network for future compression of genome sequence according to different network conditions using a reward, the reward based on at least the following:

the quality of the compression of the second genome sequence;

delays in the transmission of the second genome sequence.

Preferably, the neural network comprises an Actor-Critic algorithm to train the neural network to select or to modify the compression algorithm to improve transmission efficiency In a second aspect, the invention proposes a framework for reinforcement-learning-based network transmission model for a series of compressed genomes, comprising an Environment;

an Agent comprising a neural network; and a reward function;

the Environment including two processes;

the first process being compression of the original genome sequence of a species using a learning-based genome codec;

the second process being transmission of the compressed genome sequence of a species which is in a precedent position in the series from a sender to a receiver through a computer network;

the neural network in the Agent trained to provide an adaptive compression algorithm for the second process by observing the first process;

the Environment capable of returning a reward to the Agent to optimise the ability of the neural network to provide an adaptive compression parameter.

Preferably, the Agent is capable of selecting a compression algorithm to compress the original genome according to network conditions, thereby achieving a balance between the efficient compression and transmission of genome sequence.

Therefore, the present invention uses machine learning to build and learn a model relating different network conditions (including but not limited to bandwidths), the number of parts into which a genome sequence is divide, and the time taken for successful transmission. For example, the model is constantly being updated with data of the latest genome sequence that has just been compressed and transmitted, and the data for machine learning includes:

the length of the entire, uncompressed genome sequence that has just been transmitted successfully;

the time taken from of compressing the original genome sequence to successful transmission of the whole compressed genome sequence;

the number of parts or groups of bases (the compression parameter) that that entire original genome sequence has been divided for individual but parallel processing (this number of parts and the use of parallel processing has direct influence on the compression time);

extent of compression of each group of bases (which relates to the final file size of each compressed group of bases, and the final file size of the compressed whole genome sequence);

the bandwidth condition when the compressed genome sequence was transmitted.

It is also possible to include the extent of parallel processing as a parameter.

Therefore, for every next genome sequence, the model is able to choose how many parts the genome sequence should be divided into depending on the length of the entire genome and the network's current bandwidth, among other variables included in the machine learning, and so compress the genome sequence not too much and not too little, so that the compression extent (or ratio) is the optimal for the bandwidth.

In a second aspect, the invention proposes a framework for reinforcement-learning-based network transmission model for a series of compressed genomes, comprising an Environment;

an Agent comprising a neural network; and a reward function;

the Environment including two processes;

the first process being compression of the original genome sequence of a species using a learning-based genome codec;

the second process being transmission of the compressed genome sequence of a species which is in a precedent position in the series from a sender to a receiver through a computer network;

the neural network in the Agent being trained to provide an adaptive compression parameter for the second process by observing the first process;

the Environment capable of returning a reward to the Agent to optimise the ability of the neural network to provide an adaptive compression parameter.

Typically, the Agent is capable of selecting a compression parameter for a compression algorithm, to compress the original genome according to the current (i.e. latest known) network conditions, thereby achieving a balance between the efficient compression and transmission of genome sequence.

In other words, the invention proposes a reinforcement-learning-based network transmission model for compressed genomes, which generates adaptive compression (stride) parameter for future genomes. More specifically, the method trains a neural network model that selects a compression (stride) parameter for future genome, which is based on observations provided by the process of transmitting the last compressed genome.

Accordingly, the invention applies reinforcement learning to optimize efficiency of both compression and transmission of genome sequence. Specifically, the Agent proactively and adaptively generates compression parameters or stride parameters to adjust encoding speed and compression ratio to suit different genome sizes. This provides the possibility of achieving a balance between the efficient compression and transmission of genomes.

Experiment results show that the proposed model can be used to select a compression (stride) parameter that compresses the original genome to an extent that is appropriate for optimized transmission according to present, i.e. latest, network conditions. Therefore, the invention provides a possibility of both compressing and transmitting genome sequence to optimum, i.e. without over-optimizing any one of these processes to cause a reduction in efficiency of the other.

Embodiments of the invention may comprise the following features:

(1) Reinforcement Learning based on the transmission of compressed genomes, which generates adaptive compression (stride) parameter.

This includes training a neural network model for selecting a compression (stride) parameter for a future genome, based on observations made on the process of transmitting the latest compressed genome.

(2) A specific Environment, in which the latest compressed genome is transmitted through computer networks (i.e., in a process $P_1$) and the next genome is compressed by learning-based genome codec (i.e., in a process $P_2$).

(3) Using the Actor-Critic (A3C) approach in the training algorithm, which is a state-of-the-art actor-critic RL algorithm.

An agent state $S^a$ is defined by: data on past genome throughput, the size of the next genome, the number of genomes left to be compressed and transmitted, and the last genome compression algorithm (denoted Gob). Based on the definition of agent state $S^a$, the A3C can be applicable to train the compression algorithm so as to improve the network transmission of compressed genomes.

(4) A variety of reward goals is designed, such as to maximize the encoding speed and compression ratio for genomes (i.e., the maximization of hyper-parameters of the LEC, such as the compression parameter or stride parameter), minimize the latency in the transmissions of the compressed genome sequence in computer transmission networks, while maintaining compression speed consistency (i.e., avoiding constant Gob fluctuations or stride fluctuations).

The proposed method provides a possibility of the following advantages (for details please refer to the description of embodiments and the experimental results):

(1) it is possible to test a trained model in a simulated Environment, using network broadband datasets (i.e., network trances), RTT and noisy. In addition, the method can run experiments over mahimahi emulated network and run real-world experiments.

(2) For each species' genome sequence $g_n$, if LEC compresses the genome by using different Gobs ($GoB_1, \ldots, GoB_i$), different sizes of compressed genomes files ($x_1, \ldots, x_i$) will be generated. In other words, there is a one-to-one correspondence between $GoB_i$ and $x_i$. This means that compression is bespoke and optimised for the transmission of each genome sequence, instead of a sweeping, once-size-fits-all approach.

(3) The invention uses data from the compression of the genome of a species, particularly data on the network condition during the transmission of the compressed genome, as feed forward information to select or generate the compression algorithm for the genome of the next species.

Initially, in a process $P_1$ of an Environment, where $n-1 \geq 1$, when $n-1=1$, a default compression algorithm having predetermined quality, $\overrightarrow{GoB}_1$ is selected to be the compression algorithm $GoB_{n-1}$. The number n denotes the place of a species in a queue or series of many species, and n−1 denotes the species before.

Thus, the $1^{st}$ species' genome is compressed by using LEC with $\overrightarrow{GoB}_1$, and this first compressed genome is then transmitted through computer networks. Subsequently, the compression parameter for every next species is selected by referring to network conditions during the successful trans- mission of the species that is just one place ahead in the queue or series.

(4) When applying the invention to a simulation based on transmission dataset, instead of propagation delay, process- ing delay and queuing delay, round-trip time (RTT) may be used. The number of hidden layers, the number of filters of each convolutional layer and RTT affect the rewards for training the neural network. These parameters can be set as follows, for example, a. The number of hidden layers ranges from 1 to 3;
    b. The number of filters of each convolutional layer can be set to 4, 16, 32, 64 and 128;
    c. RTT can be set to 0 ms, 20 ms, 40 ms, 60 ms, 80 ms and 100 ms.

(4) The design and principle of adaptive stride algorithms are similar to those of the adaptive Gob algorithms.

BRIEF DESCRIPTION OF THE FIGURES

It will be convenient to further describe the present invention with respect to the accompanying drawings that illustrate possible arrangements of the invention, in which like integers refer to like parts. Other arrangements of the invention are possible, and consequently the particularity of the accompanying drawings is not to be understood as superseding the generality of the preceding description of the invention.

DETAILED DESCRIPTION OF SPECIFIC EMBODIMENTS

Figure 1:
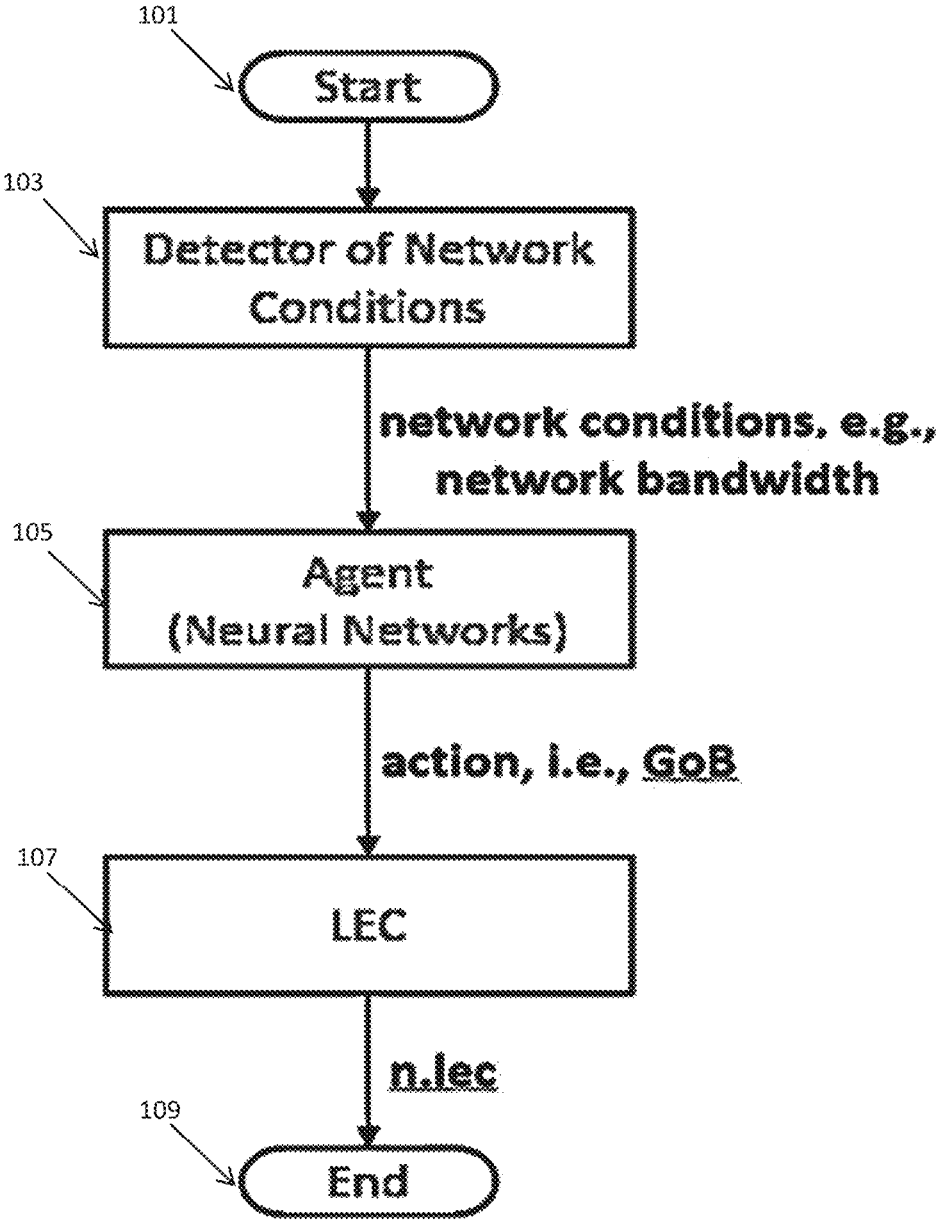
FIG. 1 is a flow chart of a method which is an embodiment of the invention.

The invention uses, but is not limited to only using, a method for compressing and encoding genome sequence which is described in US Patent U.S. Pat. No. 11,769,570 B2, This patent is owned the applicant, and has the same lead inventor. Therefore, a short description of the method will be given for completeness.

The method comprises the following steps. In a compres- sion phase, the whole genome sequence of a species is partitioned into parts called Groups of Bases. The reader should note that the acronym Gobs in U.S. Pat. No. 11,769, 570 B2 is a shorthand for "groups of bases", while the same acronym in this specification is a shorthand for the com- pression algorithm use to compress a genome sequence. The groups of bases are then processed in parallel but individu- ally, by an LEC codec that converts each group of bases into a bit stream.

Subsequently, in a transmission phase, the bit stream of each group of bases is transmitted. Since the whole genome file is composed of many sub-files (or sub-genomes), each sub-file is compressed/transmitted individually, the method is more flexible in practice.

At the receiver side, the individual bit streams are decoded back into normal uncompressed parts of the genome and concatenated to form the original genome sequence.

The number of partitions or parts into which the original genome sequence is divided is a parameter of the codec, which the user decides on and inputs, and this affects the compression ratio and the encoding speed.

In this way, a very-fast mode can be pre-set to slice the sequence data into the maximum number of groups of bases. A very-slow mode provides the highest compression ratio but with the slowest processing speed.

However, even with the method describe above, com- pressing a set of genome sequence, which is often a very big set, require a lot of process time. If such big data is overly compressed, the period of time starting from compressing the data up to successful arrival of the compressed data at the destination, could be significantly longer than a period of time required for compressing the data to only a lesser extent but transmitting so compressed data earlier.

On the other hand, under-compressed data may take less time to compress but under-compressed data could take so much time to transmit that, the total time spent is signifi- cantly more than that that would have been required to compress the data more and transmitting final, smaller file to the receiver.

The present invention relates to a reinforcement-learning- based network transmission for compressed genomes, which provides the possibility of selecting or generating adaptive compression parameters for the compression algorithms, or adaptive stride parameters, using reinforcement learning (RL).

Stride parameters refer to an alternative but different compression method, called Stride.

The present invention obtains these parameters of com- pression to determine the extent of the compression in response to transmission network conditions, so that by machine-learning, the next compression is performed only to the extent that it is optimised for the network condition.

FIG. 1 is a flowchart illustrating the overall steps of one cycle in a method of the invention. Upon starting, at 101, the method comprises a step, at 103, of using a network con- dition detector to obtain real-time network conditions, such as the current bandwidth. The network detector is simply any device which can measure or obtain information on the delays and bandwidth during a successful transmission of one set of compressed genome sequence, for a species in the queue or serial position of n−1.

Subsequently, at 105, a neural network which is call the Agent in this description, selects or generates a compression parameter, denoted Gob parameter, for compressing the genome sequence of the species next in the queue or series, in position n, based on the information just obtained by the network condition detector.

Finally, at 107, a Learning-based gEnome Codec (LEC), i.e. a compressor-decompressor module, compresses the genome sequence of that next species in position n based on the chosen or selected Gob parameter, to produce the compressed genome sequence as a file, i.e., n.lec, completing the process, at 109.

The above steps are repeated in as many cycles as needed for all the species to be compressed and transmitted, that is, starting again at step 101 for species in the queue or series position n+1, the network condition detector obtains real-time network condition during the successful transmission of the compressed genome sequence of the species in the queue or series position n.

The cycles are applied by a framework comprising an Environment, and the above-mentioned Agent which is a reinforcement-learning (RL) neural network, and which has a reward function for the Agent.

Figure 2:
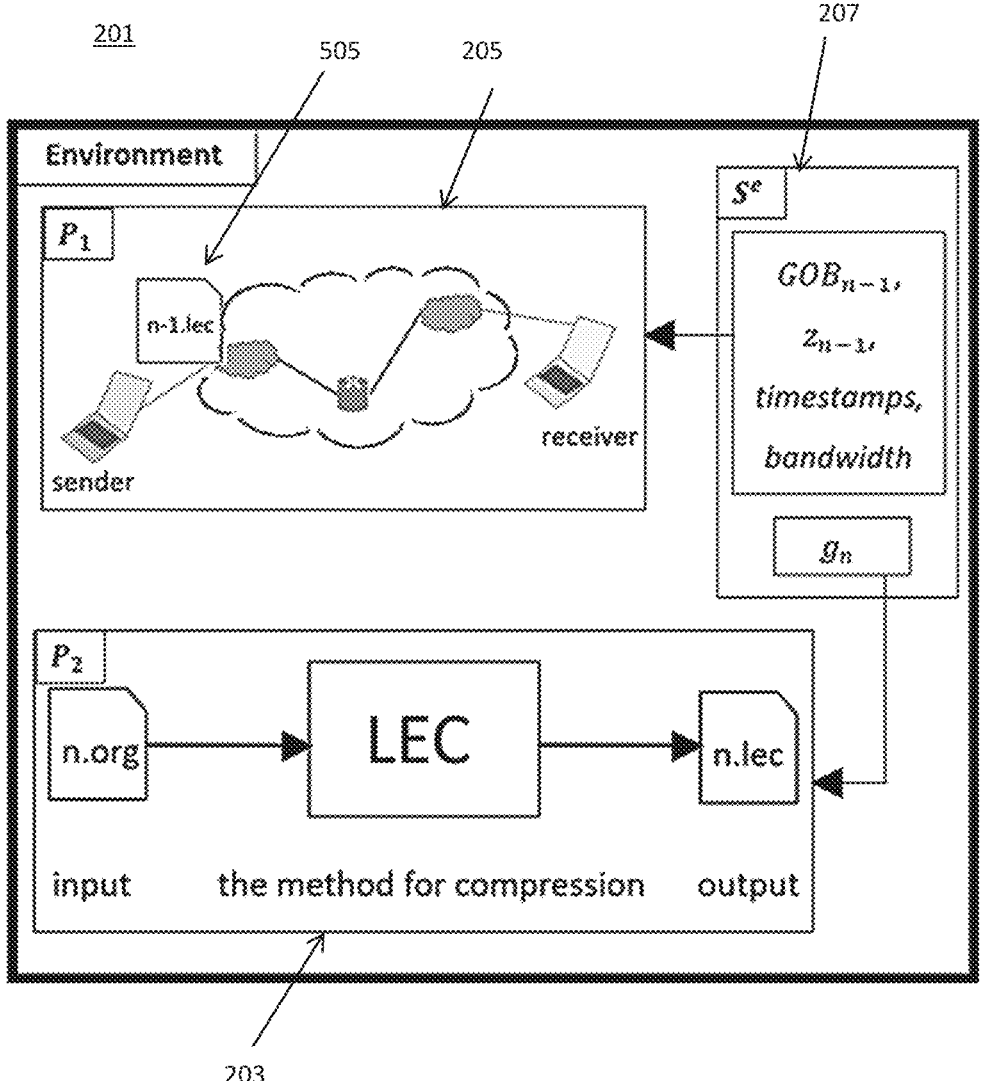
FIG. 2 is an illustration an Environment implemented in a framework applying the method of FIG. 1.

An illustration of the Environment 201 is shown in FIG. 2. Two processes are run in the Environment 201. One process 203 comprises compressing the original genome of a species using a machine learning-based genome codec, i.e. using the Gob parameter, for the current cycle. The other process 205 comprises transmitting a compressed genome sequence from a sender to a receiver through a computer network.

Figure 3:
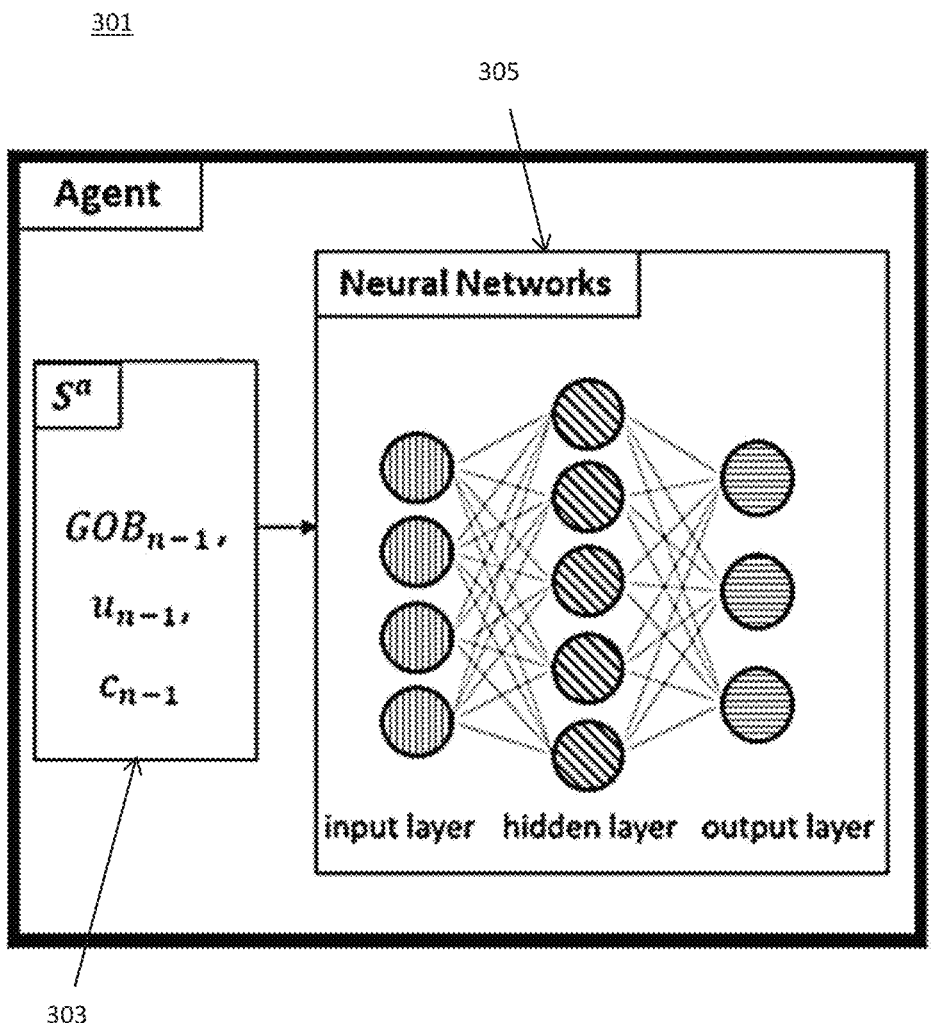
FIG. 3 is an illustration of the Agent implemented in a framework applying the method of FIG. 1.

An illustration of the Agent 301 is shown in FIG. 3. The Agent 301 provides an adaptive Gob (stride) parameter for compressing every next genome based observing the compression of each preceding genome.

Figure 4:
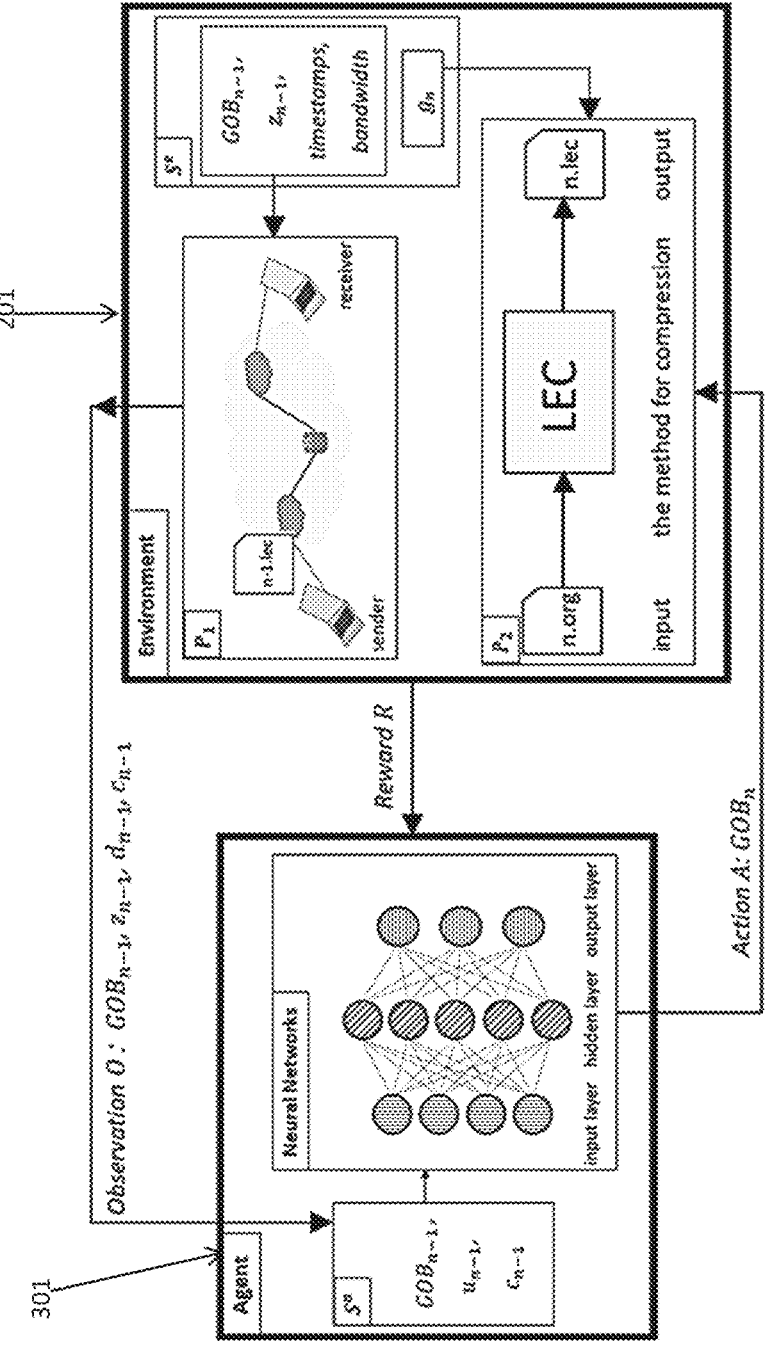
FIG. 4 illustrates the framework, and how the Environ- ment illustrated in FIG. 2 interacts with the Agent illustrated in FIG. 3.

FIG. 4 is combined of FIG. 2 and FIG. 3, and shows how information is exchanged between the Environment 201 and the Agent 301 to optimise compression of every next piece of genome sequence for optimal transmission. The reward function is denoted R, which returns a reward to the Agent 301, thereby adapting the Gob (stride) compression algorithm towards optimization.

Figure 5:
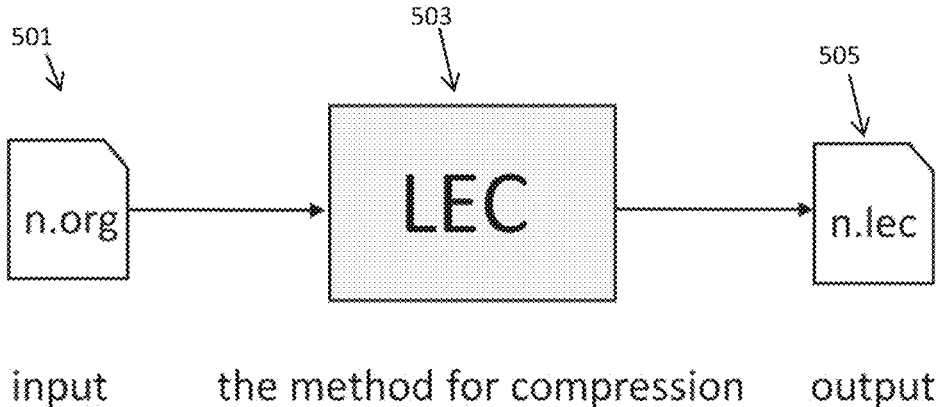
FIG. 5 is an enlargement of a process P2 shown in FIG. 2.

As mentioned, the Environment 201 comprises two processes, one process 203, $P_1$ and the other process 205, $P_2$. Specifically, $P_1$ is the process of transmitting a compressed genome of a species through network, while $P_2$ is the process of compressing an original genome of a species using learning-based genome codec (LEC). FIG. 5 is an enlarged extract of a part of FIG. 2 illustrating the process 203, $P_2$, wherein the data file of the original, uncompressed genome sequence 501 is processed be the LEC 503, which produces a file containing the compressed genome sequence 505, denoted n.lec.

$P_1$ denotes the process of transmitting the file, n−1.lec, containing the compressed genome sequence 505 of the specifies in the queue or series position n−1, i.e. the $(n-1)^{th}$ species.

For each cycle, Information and variables during process $P_1$ include:

the network conditions (e.g., the bandwidth; where each bandwidth is identified by its timestamp);

the compression algorithm Gob that has been applied to compress the genome sequence of the species ahead in the queue or series that has just been transmitted (denoted $GoB_{n-1}$ of the $(n-1)^{th}$ species); and the size of the compressed genome of the species has just been transmitted (denoted $z_{n-1}$ for the $(n-1)^{th}$ species).

These variables, including the genome sequence of the next species, i.e. the genome of the $n^{th}$ species $g_n$, are collectively called the Environment state 207, denoted $S^e$.

FIG. 4 shows the Agent 301 takes an observation O of process, $P_1$, which includes the $GoB_{n-1}$, $z_{n-1}$, any network delay during transmission of the compressed genome sequence 505 of the species $(n-1)^{th}$ denoted $d_{n-1}$, and the number of species left $c_{n-1}$ in the queue or series for genome sequence compression and transmission, and organizes the observation into an Agent state 303, denoted $S^a$.

In brief, therefore, $S^a$ includes at least the following information $GoB_{n-1}$, $c_{n-1}$, throughput of the transmission of the $(n-1)^{th}$ species $u_{n-1}$.

Specifically, the Agent state $S^a = (\overrightarrow{u}_{n-1}, \overrightarrow{x}_n, c_{n-1}, GoB_{n-1})$ where $\overrightarrow{u}_{n-1} = [u_{n-1}, u_n, \ldots, u_{n-k}]$ is the transmission throughput measurements for the past k species' genomes;

$\overrightarrow{x}_n = [x_1, x_2, \ldots, x_i]$ is a vector of i available genome sizes for the $n^{th}$ species and i denotes the number of Gobs that can be selected;

$c_{n-1}$ is the number of genomes remaining in all genomes after the genome of the $(n-1)^{th}$ species has been transmitted to the receiver; and $GoB_{n-1}$ is the Gob at which the genome sequences of the $(n-1)^{th}$ species was compressed.

FIG. 4 also illustrates that, based on information in the $S^a$, the Agent 301 performs an action A on the other process 203 in the Environment 201, $P_2$. $P_2$ is the process that compresses the genome sequence of the species next in queue or series for compression and transmission, i.e. the $n^{th}$ species. Action A refers to selecting a suitable compression parameter $GoB_n$ for the current species in the queue or serial position n.

In other words, the last-used compression parameter $GoB_{n-1}$, applied to the genome sequence of the species ahead in queue or serial position n−1 which has just been transmitted, is not presumed to be the appropriate compression parameter for the present genome sequence of the $n^{th}$ species. Instead, the proposed method is continually observing the delays in the transmission of the compressed genome sequence 505 of the species one place ahead in the queue or series, and selecting afresh the most suitable compression parameter or modifying the a compression parameter into the most suitable compression parameter, based the delays and those other information in the Agent state $S^a$.

Therefore, it can be said that the action taken by the Agent 301 is modified whenever the Environment 201 changes, and proposed provides a possibility of optimizing each compression of genomes data to achieve low transmission delay and avoid high transmission delay.

Network Delays

Figure 7:
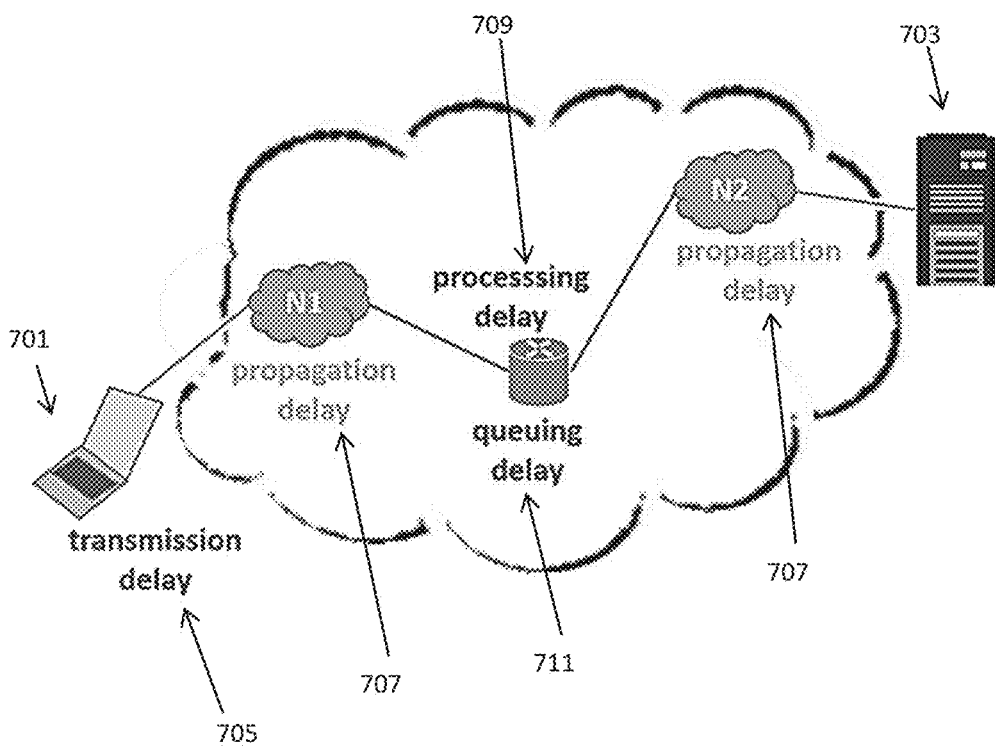
FIG. 7 is an enlargement of the illustration of the different types of delays in the transmission of the compressed genome which is possibly improved by the embodiment shown in FIG. 4.

The efficiency of a transmission is reduced by delays in the transmission. It should be noted transmission or computer network delay refers to latency in the travel of a single data bit across a network from one communication endpoint 701 to another 703. The different types of delays in the transmission are illustrated in FIG. 7.

The overall delay in a transmission is defined as the combined effect of the following four specific types of delays, i.e.

$$delay = transmission\ delay + \tag{1}$$
$$propagation\ delay + processing\ delay + queuing\ delay$$

where transmission delay 705 refers to time required to send out all packets to a transmission channel;

propagation delay 707 is time required for the packet to propagate through the channel;

processing delay 709 is the time required for routers to process the packet header; and queuing delay 711 is the time the packet takes in routing queues.

Regarding transmission delay, it may be expressed as a function, i.e.

$$transmission\ delay = \mathcal{F}(genome\ size, throughput, duration) \tag{2}$$

where $\mathcal{F}(\cdot)$ is the function, genome size is the size of the genome sequences for a species;

throughput refers to the rate of delivery over a network link (in bit/sec) of a successfully transmitted message, and duration refers to the duration time of a throughput value on the network link.

Therefore, compression reduces the size of the genome sequence, and this can reduce transmission time.

Regarding propagation delay, it may be calculated as follows, $$propagation\ delay = \frac{d}{s} \tag{3}$$

where d denotes the distance between a sender and a receiver, i.e., the link length between them; and s is the propagation speed over the specific transmission medium, e.g., the material used in network cables.

For propagation speed in wireless communication, it is deemed equal to the speed of light, and expressed as follows, $$s = c = 3 \times 10^8 \ \frac{m}{s} \tag{4}$$

Equations (3) and (4) show how it has been taken into consideration that propagation delay varies with propagation medium and link length.

The Reinforcement Learning (RL) Agent 301

Figure 6:
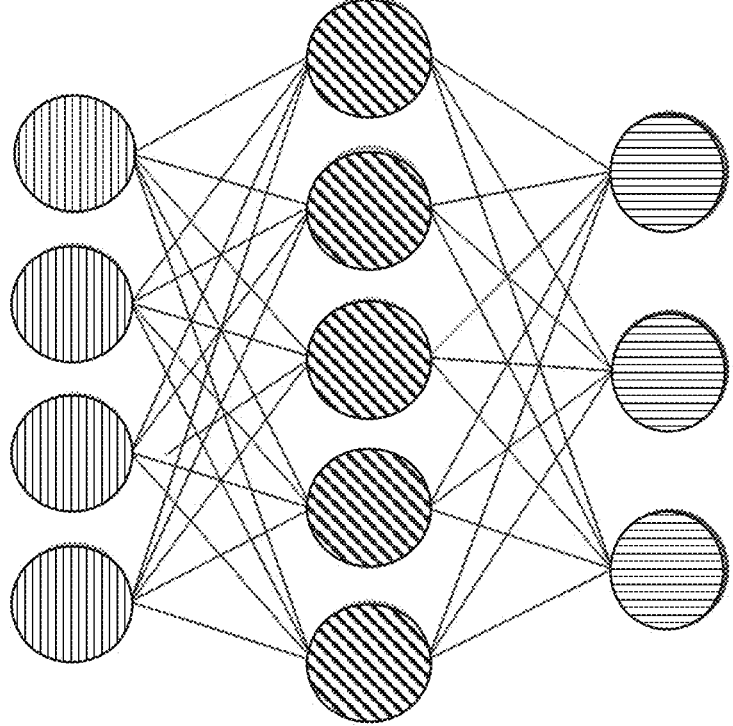
FIG. 6 is an enlargement of the illustration of the neural network shown in FIG. 3.
Figure 8:
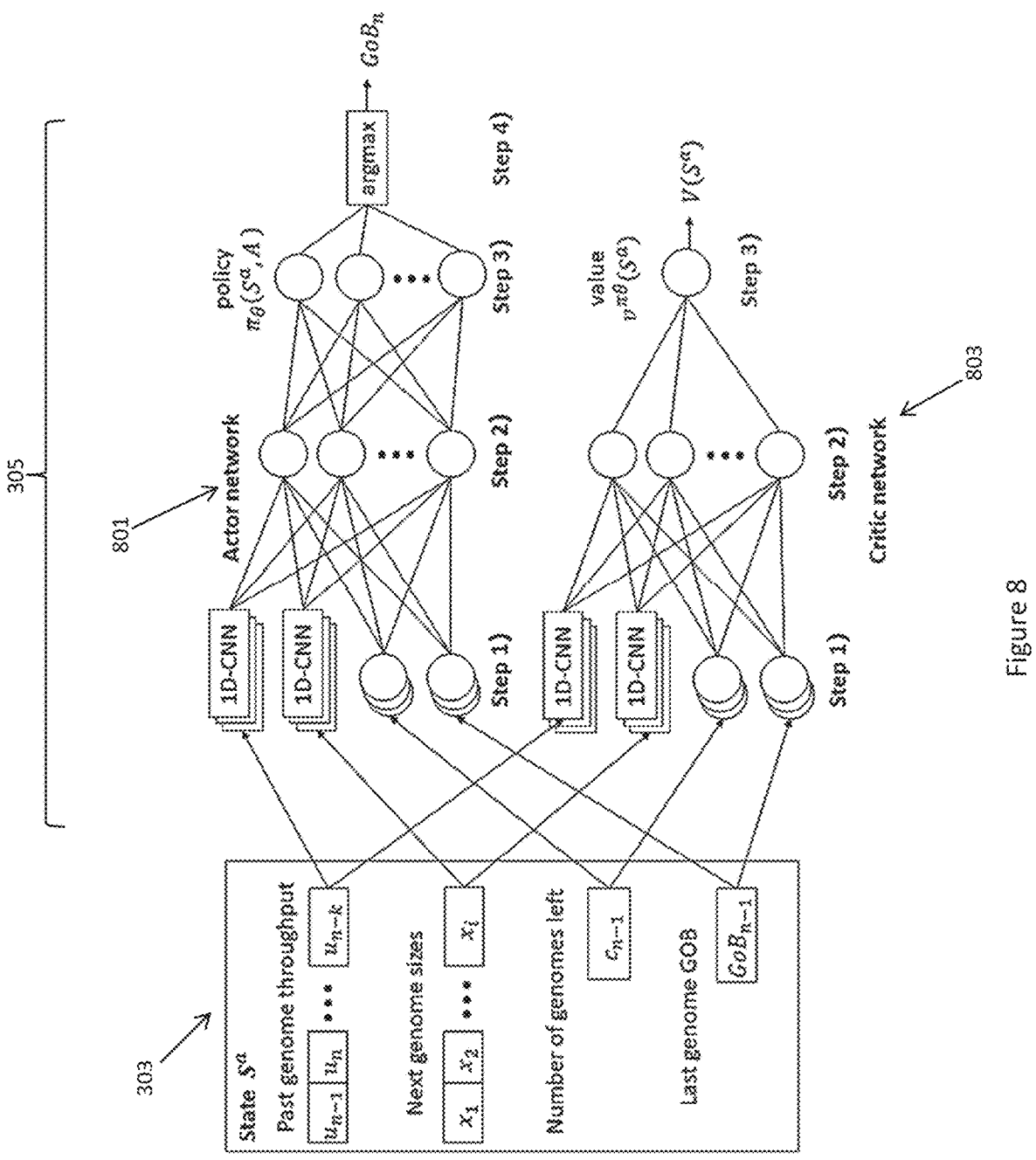
FIG. 8 illustrates in greater detail the neural network in the Agent illustrated in FIG. 3.

FIG. 8 is an illustration of a design of the Agent 301, i.e. a neural network that generates adaptive Gob policies. FIG. 6 an enlargement of the illustration of the neural network shown in FIG. 3, showing the neural network has an input layer, a hidden layer and an output layer.

When the genome sequence of the preceding species, the $(n-1)^{th}$ species, has been compressed by an LEC 503, the Agent 301 inputs the Agent state $S^a$ to the neural network 305.

Preferably, the neural network comprises an Actor-Critic algorithm (A3C). A3C is a state-of-the-art Actor-Critic method, which consists of an Actor neural network 801 and a Critic neural network 803. Given an array of available Gobs, i.e. $\overrightarrow{GoB}=[GoB_1, \ldots, GoB_i]$ or an array of available strides, i.e. $\overrightarrow{str}=[str_1, \ldots, str_j]$, the A3C) can be used to generate adaptive Gob policies or adaptive stride policies.

On receiving Agent state $S^a=(\overrightarrow{u_{n-1}}, \overrightarrow{x_n}, c_{n-1}, GoB_{n-1})$, the Actor neural network 801 begins to learn a policy, and takes an action A that corresponds to the Gob for compressing the genome of the present species, i.e. the $n^{th}$ species). Specifically, the following steps are executed.

1) $\overrightarrow{u_{n-1}}$ and $\overrightarrow{x_n}$ are fed into a 1-dimensional convolution layer (CNN) with 128 filters, respectively. The size of each filter is 4 and the convolution stride is 1. $c_{n-1}$ and $GoB_{n-1}$ are input to a 128-dimensional fully connected layer with a ReLU activation function, respectively.

2) The four outputs are concatenated as a vector, which is fed to a fully connected layer with a ReLU function to generate a 128-dimensional vector $\overrightarrow{o}=[o_1, o_2, \ldots, o_i]$.

3) The vector is then fed into a fully connected layer with a softmax function to produce a i-dimensional vector $\overrightarrow{p}=[p_1, p_2, \ldots, p_i]$, where $p_1+p_2+ \ldots +p_i=1$. The softmax function is a normalized exponential function, which is defined as follows, $$softmax(\vec{o}) = \frac{e^{o_i}}{\sum e^{o_i}} \tag{7}$$

The index of the largest probability $p_l$ in the array $\overrightarrow{p}$ (i.e., l) is computed.

Subsequently, l and $\overrightarrow{GoB}$ are used to obtain the adaptive Gob for the present $n^{th}$ genome (i.e., $GoB_n$). This may be expressed as, $$l = argmax(\vec{p}) = argmax([p_1, p_2, \ldots, p_i]) \tag{8}$$
$$GoB_n = \overrightarrow{GoB_l} \tag{9}$$

where argmax($\cdot$) is a function for calculating the index of the largest value in an array.

In short, the policy can be described with a probability distribution over actions and states as follows, $$\pi_\theta(S^a, A) \to [0,1] \tag{10}$$

where $\pi_\theta(S^a, A)$ is the probability that action A is taken under current state $S^a$, ranging from 0 to 1, and $\theta$ is the learnable parameters of the Actor neural network.

Step 1) and step 2) in the Critic neural network 803 are similar to step 1) and step 2) in the Actor neural network, and do not need to be described again.

In step 3) of the Critic neural network 803, the 128-dimensional vector (i.e., the output of step 2)) is fed into a linear neuron (without activation function) to generate a value $V(S^a)$. If faced with two states, the reinforcement-learning (RL) neural network, i.e. the Agent 301, compares the values of the two states and then takes the better policy.

A value function is then designed according to the policy, which is defined as $v^{\pi\theta}(s_t)$, where $\pi_\theta(\cdot)$ denotes the policy function.

Design of the Reward Function

After applying each action A, the Environment 201 provides the Agent 301 with a reward, R, for that training data. Moreover, the Agent 301 aims to maximize the expected and cumulative rewards as follows:

$$\mathcal{R} = \max\sum R_n \qquad (11)$$

The reward is designed to reflect the performance of the network transmission of each species' genome according to the following factors:

1) the Gob used for compressing the genome of the species;
2) the observed latency of the compressed genome in the network transmission.

Based on this, the reward for the $n^{th}$ species' genome is given as follows, $$R_n = \qquad (12)$$

$$q(GoB_n) - \text{penalty}_{delay} * \text{delay}_n - \text{penalty}_{smooth} * |q(GoB_n) - q(GoB_{n-1})|$$

where $q(\cdot)$ is a quality evaluation function mapping that $GoB_n$ to the quality perceived by a user;
$|\cdot|$ is an absolute value function;
$\text{penalty}_{delay}$ and $\text{penalty}_{smooth}$ are hyperparameters;
$GoB_n$ is an adaptive Gob used for the compression of the $n^{th}$ species' genome;
$\text{delay}_n$ denotes network latency of transmitting the $n^{th}$ species' genome.

Generally, there are two kinds of quality evaluation functions, a linear function and a log function. The reward function using linear quality evaluation is expressed as follows, $$R_n = GoB_n - \text{penalty}_{delay} * \text{delay}_n - \text{penalty}_{smooth} * |GoB_n - GoB_{n-1}| \qquad (13)$$

$$\text{where } q(GoB_n) = GoB_n.$$

The reward function using log quality evaluation is expressed as follows, $$R_n = \log(GoB_n) - \text{penalty}_{delay} * \text{delay}_n - \qquad (14)$$

$$\text{penalty}_{smooth} * |\log(GoB_n) - \log(GoB_{n-1})|$$

$$\text{where } (GoB_n) = \log(GoB_n).$$

While there has been described in the foregoing description preferred embodiments of the present invention, it will be understood by those skilled in the technology concerned that many variations or modifications in details of design, construction or operation may be made without departing from the scope of the present invention as claimed.

Experiment Results

The proposed method has been evaluated using a simulated but realistic network situations, using broadband dataset that the Federal Communications Commission (FCC) collected in 2018. The records of network traces in the FCC broadband dataset consist of timestamps and bandwidths, where the former is in MB/sec and the latter is in seconds. In addition, random noise is added to each transmission of compressed genome sequence 505 to emulate real-world computer networks.

However, processing delays and queuing delays in a computer network are not easily available data. Therefore, instead of propagation delay, processing delay and queuing delay, the evaluation uses round-trip time (RTT) instead of the delay equation (1). RTT does not include transmission delay but includes the other three kinds of delays. There, RTT is defined as follows, $$RTT = \text{propagation delay} + \text{processing delay} + \text{queuing delay} \qquad (5)$$

The RTT may be given a fixed value, e.g., 80 milliseconds. Therefore, based on the previous analysis for network delay and RTT, the combined propagation delay, processing delay and queuing delay can be replaced with RTT.

Finally, network delay is described with transmission delay and RTT as follows, $$\text{delay} = \text{transmission delay} + RTT \qquad (6)$$

The variables throughput (in bit/sec) and duration required for calculating transmission delays can be obtained from the broadband dataset.

Figure 9:
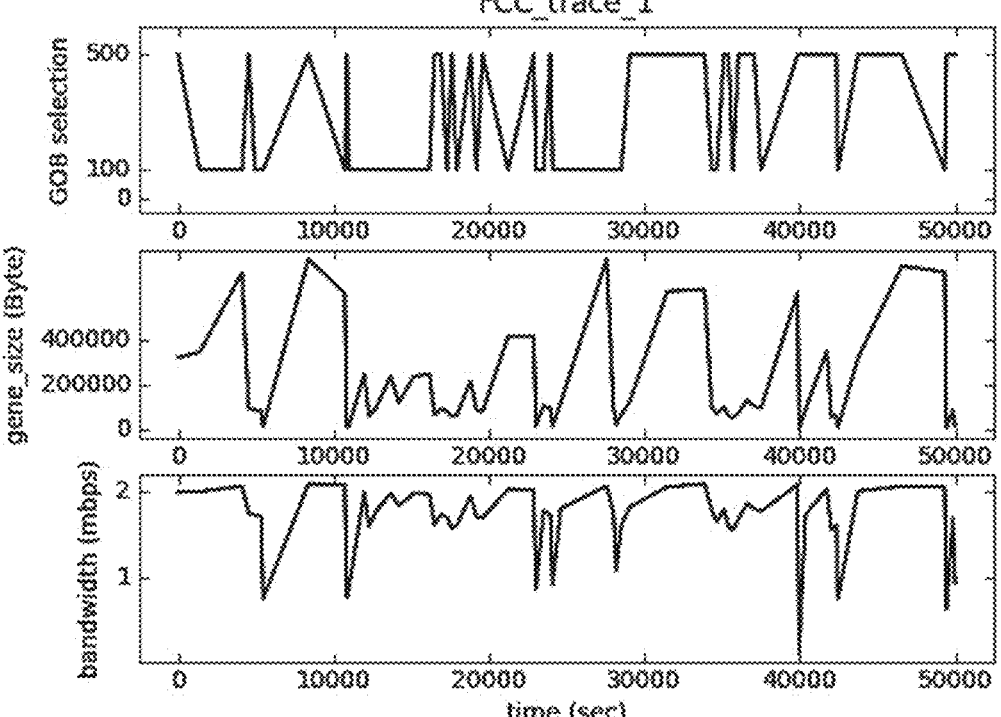
FIG. 9 show the transmissions of compressed genomes files observed when the proposed method is applied to a FCC wideband dataset.

FIG. 9 show the transmissions of compressed genomes files observed when the proposed method is applied to the FCC wideband dataset. The abscissa represents time. The ordinate of the first subfigure is selected GOB, the ordinate in the second subfigure is genome size, and the ordinate in the third subfigure is the actual bandwidth of the network.

It can be seen that actual bandwidths in the network changes over time, but the proposed method is able to select an appropriate GOB in response to the current bandwidth.

The compressed gene sizes are shown in middle subgraph. The fluctuations in the size of the compressed genomes are basically consistent with the fluctuations in the actual network bandwidth. This shows that the choice of GOB made by the proposed method reflects the state of the bandwidth reasonably, and is therefore effective.

The invention claimed is:

1. A method of transmitting a genome sequence among a series of genome sequences, comprising the steps of:
   a) obtaining network condition data during a transmission of compressed form of a first genome sequence precedent in the series;
   b) selecting a compression algorithm or modifying a compression parameter based on the network condition data; which includes
      supplying the network condition data to a neural network; such that
      the neural network selects the compression parameter or modifies the compression algorithm;
      the neural network trained using training data that includes variables of past transmissions;

the variables of each past transmission include at least the following:

network conditions of transmitting the compressed genome sequence;

'compression algorithm used to compress the genome sequence;

the size of the compressed genome sequence;

c) compressing a second genome sequence which is next in the series using the selected or modified compression parameter, to obtain a compressed form of the second genome sequence; and d) transmitting the compressed form of the second set genome; and e) adapting the neural network for future compression of genome sequence according to different network conditions using a reward, the reward based on at least the following:

the quality of the compression of the second genome sequence; and delays in the transmission of the second genome sequence.

2. A method of transmitting a genome sequence among a series of genome sequences, as claimed in claim 1, wherein the neural network comprises an Actor-Critic algorithm to train the neural network to select or to modify the compression algorithm to improve transmission efficiency.

3. A framework system for a reinforcement-learning-based network transmission model for a series of compressed genomes, the system comprising:

a compressor-decompressor module;

a network condition detector;

an Environment;

an Agent comprising a neural network; and a reward function;

the Environment including two processes;

the compressor-decompressor module configured for the first process of compressing of a species' original genome sequence using a learning-based genome codec;

the network transmission configured for the second process of transmitting the compressed genome sequence of a species which is in a precedent position in the series from a sender to a receiver through a computer network;

the neural network in the Agent trained to provide an adaptive compression algorithm for the second process by observing the first process; and the Environment capable of returning a reward to the Agent to optimise the ability of the neural network to provide an adaptive compression parameter.

4. A framework for a reinforcement-learning-based network transmission model for compressed genomes as claimed in claim 3, wherein the Agent is capable of selecting a compression algorithm to compress the original genome according to network conditions, thereby achieving a balance between the efficient compression and transmission of genome sequence.

* * * * *